US012611194B2

(12) United States Patent
Tanaka

(10) Patent No.: US 12,611,194 B2
(45) Date of Patent: Apr. 28, 2026

(54) ULTRASOUND DIAGNOSTIC APPARATUS FORMING ULTRASOUND IMAGE BASED ON RF SIGNALS SUBJECTED TO SIGNAL PROCESSING IN CONSIDERATION OF TARGET REGION

(71) Applicant: FUJIFILM Healthcare Corporation, Chiba (JP)

(72) Inventor: Chizue Tanaka, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 42 days.

(21) Appl. No.: 18/391,706

(22) Filed: Dec. 21, 2023

(65) Prior Publication Data

US 2024/0206855 A1 Jun. 27, 2024

(30) Foreign Application Priority Data

Dec. 26, 2022 (JP) ................................. 2022-207981

(51) Int. Cl.
*A61B 8/00* (2006.01)

(52) U.S. Cl.
CPC .......... *A61B 8/5269* (2013.01); *A61B 8/5207* (2013.01)

(58) Field of Classification Search
CPC ....... A61B 8/469; A61B 8/461; A61B 8/5269; A61B 8/5246; G01S 15/8981; G01S 7/52084; G01S 7/52077
See application file for complete search history.

(56) References Cited

U.S. PATENT DOCUMENTS

2012/0310087 A1* 12/2012 Miyaki .................. A61B 8/485
                                                    600/440
2014/0187947 A1* 7/2014 Hansegard ............. A61B 8/469
                                                    600/443

2018/0242951 A1* 8/2018 Hiroshima .......... G01S 7/52026
2019/0083068 A1* 3/2019 Sornes ................. A61B 8/5253
2019/0261953 A1* 8/2019 Honjo ....................... A61B 8/15
2019/0328364 A1* 10/2019 Questa .................. A61B 8/485
2019/0336106 A1* 11/2019 Kozai .................. A61B 8/5207
2020/0281570 A1 9/2020 Sato et al.
2021/0007712 A1* 1/2021 Fuse ...................... A61B 8/54
2021/0312594 A1 10/2021 Yamanaka et al.
2021/0345989 A1* 11/2021 Hancock .................. A61B 8/12
2024/0404066 A1* 12/2024 Weber ...................... G06T 7/11

FOREIGN PATENT DOCUMENTS

JP       2020114294       7/2020
JP       2021159511       10/2021

* cited by examiner

*Primary Examiner* — Nyrobi Celestine

(74) *Attorney, Agent, or Firm* — JCIPRNET

(57) ABSTRACT

A target region specifying unit specifies a target region corresponding to an object in a subject in a data space of an RF signal, by analyzing ultrasound data, which is at least one of the RF signal transmitted from a transmission/reception unit, a coordinate transformation signal transmitted from an image formation unit, or an ultrasound image (B-mode image) transmitted from the image formation unit. A signal processing unit executes normal signal processing, which is signal processing according to a depth of the subject, with respect to the RF signal outside the target region (that is, RF signal in a non-target region) and executes specific signal processing different from the normal signal processing with respect to the RF signal inside the target region. The image formation unit forms the ultrasound image based on the RF signal subjected to the signal processing by the signal processing unit.

5 Claims, 5 Drawing Sheets

AZIMUTH
DIRECTION

DEPTH
DIRECTION

NTA

TAa

Rb

ULTRASOUND DIAGNOSTIC APPARATUS FORMING ULTRASOUND IMAGE BASED ON RF SIGNALS SUBJECTED TO SIGNAL PROCESSING IN CONSIDERATION OF TARGET REGION

CROSS-REFERENCE TO RELATED APPLICATION

This application claims the priority benefits of Japanese application no. 2022-207981, filed on Dec. 26, 2022. The entirety of the above-mentioned patent application is hereby incorporated by reference herein and made a part of this specification.

BACKGROUND

1. Technical Field

The present specification discloses an improvement of an ultrasound diagnostic apparatus.

2. Description of the Related Art

In the related art, an ultrasound' diagnostic apparatus has been known, which transmits and receives ultrasound waves to and from a subject, forms an ultrasound image based on a reception signal obtained by transmitting and receiving the ultrasound waves, and displays the formed ultrasound image on a display. In the ultrasound diagnostic apparatus, an examiner can obtain an appropriate image for diagnosis only after adjusting an imaging parameter of an ultrasound probe or an apparatus main body to an appropriate value according to a patient or an imaging part.

For example, JP2020-114294A or JP2021-159511A discloses an ultrasound diagnostic apparatus that can automatically apply appropriate image quality improvement processing based on a change in a signal amount of a subject. In these apparatuses, it is possible to improve a signal-to-noise ratio (S/N ratio) particularly according to a depth-dependent change in an echo signal from the subject. In this way, by improving the image quality according to an examination scene, the diagnostic performance is improved or the examination time is shortened.

SUMMARY

In some cases, various objects are present in an imaging region (range) of the ultrasound image. Typical examples of the object include an organ and a blood vessel. For example, during abdominal imaging, various organs, such as stomach, liver, kidney, gallbladder, blood vessel, intestinal tract, and pancreas, are often imaged at the same time. Here, in some cases, a position or a depth of the object differs depending on the subject or an imaging cross section, and a desired image quality may differ for each object. For example, the visibility of a lumen is required in the gallbladder, and deep sensitivity is required in the pancreas. Since the intensity of the echo signal from each object differs depending on the subject, in a case in which the image quality improvement processing is performed based only on the change in the signal amount, there is a possibility that the image quality improvement processing suitable for each object cannot be performed.

An object of an ultrasound diagnostic apparatus disclosed in the present specification is to provide an ultrasound diagnostic apparatus that can enhance an image quality of an ultrasound image also in consideration of a target region corresponding to an object in a subject, in addition to a depth of the subject.

An aspect of the present specification relates to an ultrasound diagnostic apparatus comprising: a target region specifying unit that specifies a target region corresponding to an object in a subject in a data space of an RF signal obtained by transmitting and receiving ultrasound waves to and from the subject, by analyzing ultrasound data or based on an indication by a user with respect to an ultrasound image, the ultrasound data being at least one of the RF signal, a coordinate transformation signal obtained by transforming the RF signal into data on a coordinate space of the ultrasound image, or the ultrasound image formed based on the coordinate transformation signal; a signal processing unit that executes signal processing with respect to the RF signal, the signal processing unit executing normal signal processing, which is signal processing according to a depth of the subject, with respect to the RF signal outside the target region and executing specific signal processing different from the normal signal processing with respect to the RF signal inside the target region; and an image formation unit that forms the ultrasound image based on the RF signal subjected to the signal processing by the signal processing unit.

With this configuration, the signal processing having different contents is executed between the RF signal inside the target region corresponding to the object of the subject and the RF signal outside the target region. As a result, in a region outside the target region, it is possible to execute the normal signal processing according to the depth of the subject, and it is possible to realize the image quality required for the object. That is, it is possible to enhance the image quality of the ultrasound image also in consideration of the target region corresponding to the object in the subject, in addition to the depth of the subject.

The target region specifying unit may specify a type of the object corresponding to the specified target region, and in a case in which the type of the object is specified, the signal processing unit may execute the specific signal processing according to the specified type of the object with respect to the RF signal inside the target region.

With this configuration, the specific signal processing according to the type of the object can be executed.

In a case in which the type of the object is not specified, the signal processing unit may execute predetermined specific signal processing with respect to the RF signal inside the target region.

With this configuration, in a case in which the type of the object is not specified, the predetermined specific signal processing can be executed.

The ultrasound diagnostic apparatus may further comprise a region transformation unit that transforms the target region, which is specified based on the coordinate transformation signal, the ultrasound image, or the indication by the user, in the coordinate space of the ultrasound image into the target region in the data space of the RF signal.

With this configuration, even in a case in which the target region is specified in the coordinate space of the ultrasound image, this target region can be transformed into the target region in the data space of the RF signal.

The signal processing unit may also execute the normal signal processing with respect to the RF signal inside the target region, and the image formation unit may synthesize the ultrasound image formed based on the RF signal subjected to the normal signal processing and the ultrasound image formed based on the RF signal subjected to the specific signal processing for the inside of the target region at a synthesis ratio indicated by the user.

With this configuration, the user can synthesize the ultrasound image formed based on the RF signal subjected to the normal signal processing and the ultrasound image formed based on the RF signal subjected to the specific signal processing at any synthesis ratio.

With the ultrasound diagnostic apparatus disclosed in the present specification, it is possible to enhance the image quality of the ultrasound image also in consideration of the target region corresponding to the object in the subject, in addition to the depth of the subject.

DESCRIPTION OF THE EMBODIMENTS

Figure 1:
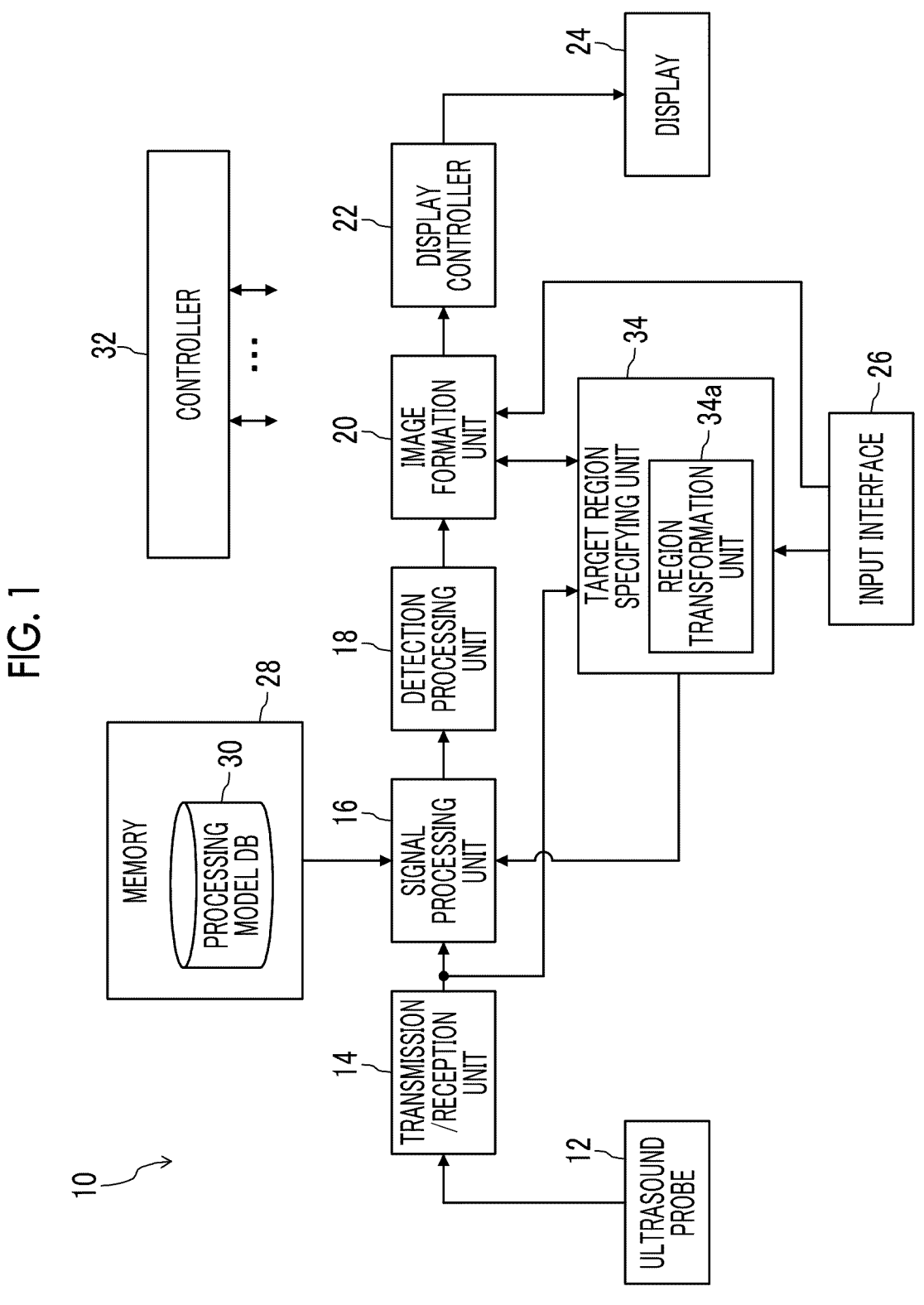
FIG. 1 is a schematic configuration diagram of an ultrasound diagnostic apparatus according to the present embodiment.

FIG. 1 is a schematic configuration diagram of an ultrasound diagnostic apparatus 10 according to the present embodiment. The ultrasound diagnostic apparatus 10 is a medical apparatus that is installed in a medical institution, such as a hospital, and is used during an ultrasound examination.

The ultrasound diagnostic apparatus 10 is an apparatus that scans a subject with an ultrasound beam to generate an ultrasound image based on a reception signal obtained by the scanning. For example, the ultrasound diagnostic apparatus 10 forms a tomographic image (B-mode image) in which the amplitude intensity of reflected waves from a scanning surface is transformed into the brightness based on the reception signal. Alternatively, the ultrasound diagnostic apparatus 10 can also form a Doppler image, which is an ultrasound image showing a motion velocity of a tissue in the subject, based on a difference (Doppler shift) between frequencies of transmitted waves and received waves. In the present embodiment, processing of generating the B-mode image by the ultrasound diagnostic apparatus 10 will be described.

An ultrasound probe 12 is a device that transmits and receives ultrasound waves to and from the subject. The ultrasound probe 12 has an oscillation element array including a plurality of oscillation elements that transmit and receive the ultrasound waves to and from the subject.

A transmission/reception unit 14 transmits a transmission signal to the ultrasound probe 12 (specifically, each oscillation element of the oscillation element array) under the control of a controller 32 (described later). As a result, the ultrasound waves are transmitted from each oscillation element toward the subject. In addition, the transmission/reception unit 14 receives a reception signal from each oscillation element that receives the reflected waves from the subject. The transmission/reception unit 14 includes an adder and a plurality of delayers corresponding to the respective oscillation elements, and phase adjustment addition processing of aligning and adding phases of the reception signals from the respective oscillation elements is performed by the adder and the plurality of delayers. As a result, reception beam data in which information indicating the signal intensity of the reflected waves from the subject is arranged in a depth direction of the subject is formed. In the present specification, the reception beam data before being transformed into data on a coordinate space of the ultrasound image by an image formation unit 20 described later is referred to as a radio frequency (RF) signal.

The RF signal as ultrasound data is transmitted to a target region specifying unit 34 described later.

The signal processing unit 16 executes various types of signal processing including, for example, filter processing of applying a bandpass filter to the RF signal from the transmission/reception unit 14. In particular, the signal processing unit 16 executes different signal processing between the RF signal inside a target region specified by the target region specifying unit 34 described in detail later and the RF signal outside the target region.

A detection processing unit 18 executes processing, such as detection processing (for example, envelope detection processing) or logarithmic compression processing, with respect to the RF signal after the processing by the signal processing unit 16. The RF signal loses the phase information (frequency information) due to the detection processing by the detection processing unit 18. That is, an amount of information of the RF signal after the detection processing is smaller than an amount of information of the RF signal before the detection processing.

An image formation unit 20 forms the ultrasound image (B-mode image) based on the RF signal subjected to the detection processing or the like by the detection processing unit 18. First, the image formation unit 20 transforms the RF signal into the data on the coordinate space of the ultrasound image. In the present specification, the data after the transformation is referred to as a coordinate transformation signal. Then, the image formation unit 20 forms the ultrasound image (B-mode image) based on the coordinate transformation signal. The coordinate transformation signal or the ultrasound image as the ultrasound data is transmitted to the target region specifying unit 34 described later.

A display controller 22 performs control of displaying, on a display 24, the ultrasound image formed by the image formation unit 20 and various types of other information. The display 24 is, for example, a display device configured of a liquid crystal display, an organic electro luminescence (EL), or the like.

An input interface 26 is configured of, for example, a button, a track ball, a touch panel, or the like. The input interface 26 is used to input a command from a user to the ultrasound diagnostic apparatus 10.

A memory 28 includes a hard disk drive (HDD), a solid state drive (SSD), an embedded multi media card (eMMC), a read only memory (ROM), or the like. The memory 28 stores an ultrasound diagnostic program for operating each of the units of the ultrasound diagnostic apparatus 10. It should be noted that the ultrasound diagnostic program can also be stored, for example, in a computer-readable non-transitory storage medium, such as a universal serial bus (USB) memory or a CD-ROM. The ultrasound diagnostic apparatus 10 can read and execute the ultrasound diagnostic program from such a storage medium.

Further, as shown in FIG. 1, a processing model database (DB) 30 is stored in the memory 28. The processing model DB 30 is a database in which a type of an object (for example, organ or blood vessel) and a processing content are associated with each other. The processing model DB 30 is created in advance by a designer of the ultrasound diagnostic apparatus 10 or the like, and is stored in the memory 28. Details of the contents of the processing model DB 30 and the method of using the same will be described later.

The controller 32 includes at least one of a general-purpose processor (for example, a central processing unit (CPU)) or a dedicated processor (for example, a graphics processing unit (GPU), an application specific integrated circuit (ASIC), a field-programmable gate array (FPGA), a programmable logic device, and the like). The controller 32 may be configured by the cooperation of a plurality of processing devices that are present at physically separated positions, instead of being configured of one processing device. The controller 32 controls each of the units of the ultrasound diagnostic apparatus 10 according to the ultrasound diagnostic program stored in the memory 28.

The target region specifying unit 34 specifies the target region corresponding to the object in the subject in the data space of the RF signal, by analyzing the ultrasound data, which is at least one of the RF signal transmitted from the transmission/reception unit 14, the coordinate transformation signal transmitted from the image formation unit 20, or the ultrasound image (B-mode image) transmitted from the image formation unit 20.

In the present embodiment, the target region specifying unit 34 specifies the target region by using a learning device trained, by using the ultrasound data including the object as input data and information indicating a position of the object in the ultrasound data as teacher data, to specify the position of the object included in the ultrasound data from features of the input ultrasound data. The learning device need only be trained in advance and stored in the memory 28.

In addition, the learning device may be trained by using the ultrasound data from the object as the input data and information indicating the type (for example, liver or pancreas) of the object included in the ultrasound data as the teacher data, in addition to the information indicating the position of the object in the ultrasound data. By using such a learning device, the target region specifying unit 34 can specify the type (specifically, what the object is) of the object, in addition to the position (target region) of the object, in the data space of the RF signal.

Figure 2:
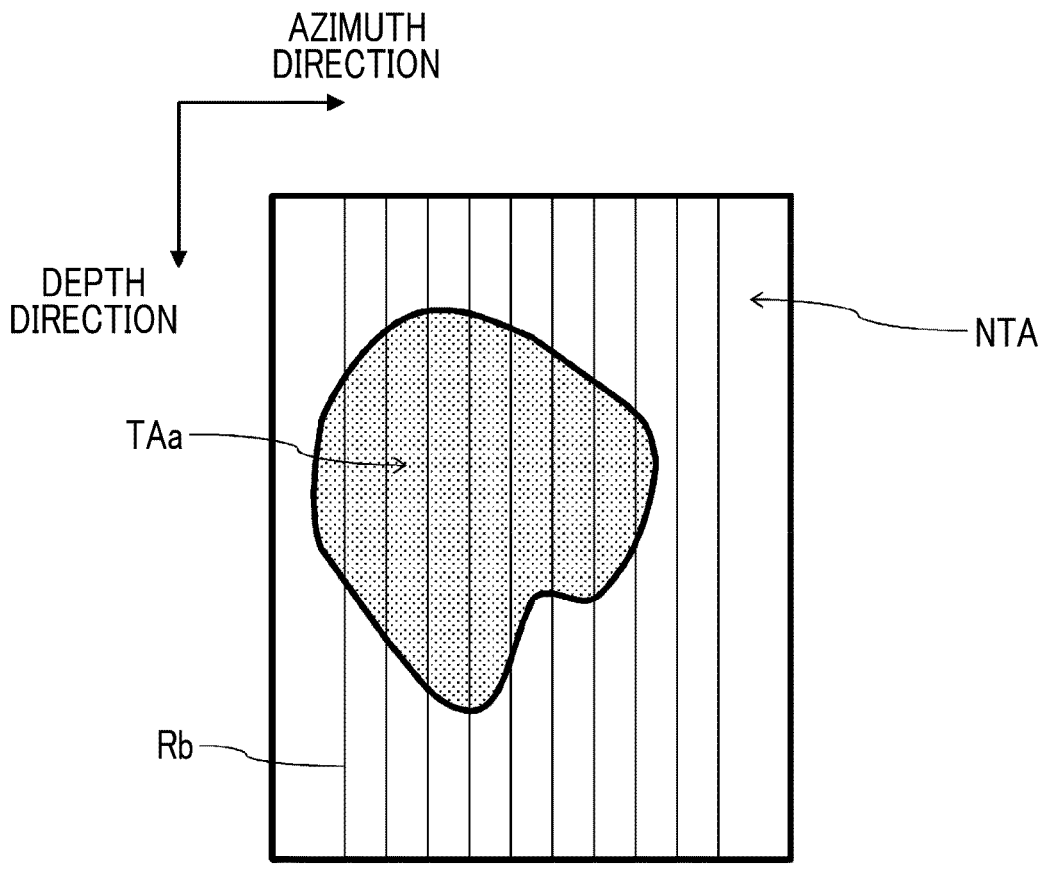
FIG. 2 is a conceptual diagram showing a target region specified in a data space of an RF signal.

FIG. 2 shows a target region TAa, which is specified by the target region specifying unit 34, in the data space of the RF signal defined in a depth direction and an azimuth direction. In FIG. 2, the target region TAa is shaded. In the present specification, a region other than the target region TAa is referred to as a non-target region NTA. In addition, in FIG. 2, a line extending in the depth direction represents reception beam data Rb.

Figure 3:
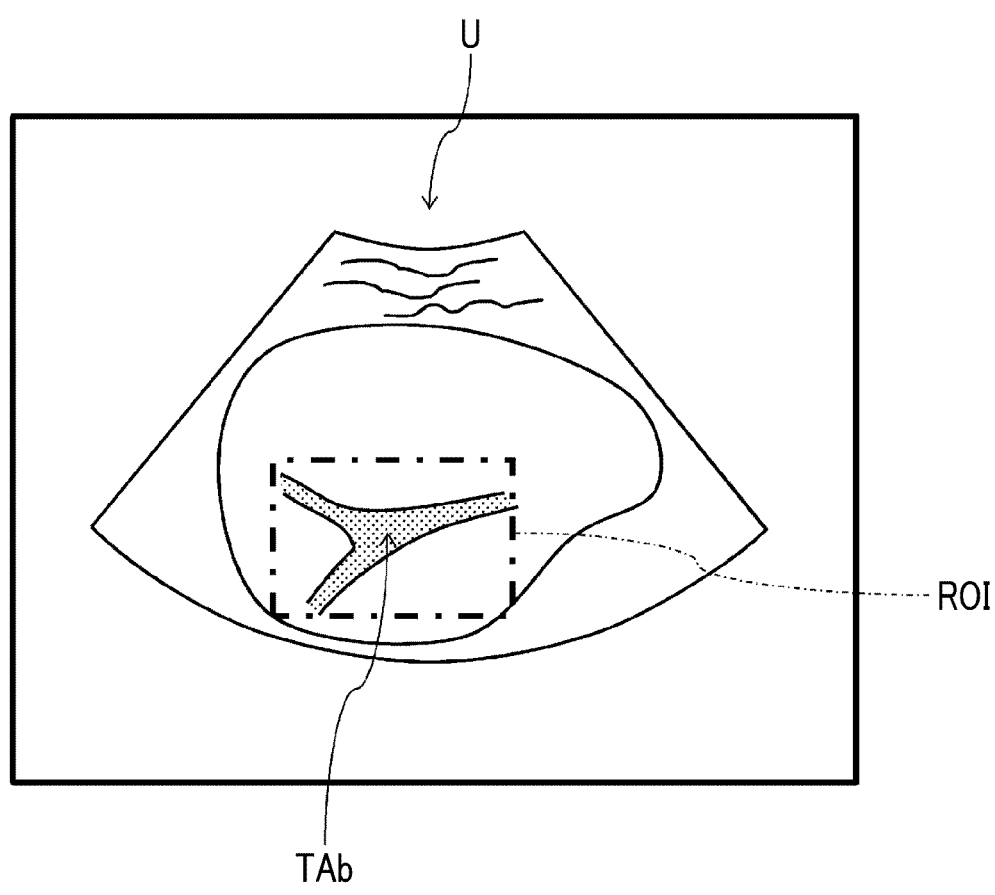
FIG. 3 is a diagram showing a region of interest and the target region in an ultrasound image.

The target region TAa can be specified by the target region specifying unit 34 by a method other than the method using the learning device described above. For example, as shown in FIG. 3, in an ultrasound image U displayed on the display 24, the user sets a region of interest ROI including the object (here, blood vessel) by using the input interface 26. It may be possible to designate the region of interest ROI, for example, by an organ name or the like, instead of being set by a rectangle or the like as shown in FIG. 3. The target region specifying unit 34 can specify a target region TAb on the ultrasound image U by detecting the object in the set region of interest ROI. A region transformation unit 34*a* described later transforms the target region TAb on the ultrasound image U into the target region TAa in the data space of the RF signal. It should be noted that, since a known method can be adopted as a method of detecting the object in the region of interest ROI, the detailed description thereof will be omitted here. In a case in which there is no object in the region of interest ROI, the target region specifying unit 34 need only output an error. In addition, the target region specifying unit 34 may output a notification prompting the user to set the region of interest ROI again after outputting the error.

In addition, the user may directly designate the object on the ultrasound image U, instead of the region of interest ROI. For example, the user designates a contour of the object on the ultrasound image U by using the input interface 26. The target region specifying unit 34 specifies the region designated in this way as the target region TAb on the ultrasound image U.

In a case in which the target region specifying unit 34 specifies the target region TAb on the coordinate space of the ultrasound image U based on the coordinate transformation signal or the ultrasound image or based on an indication by the user with respect to the ultrasound image U, the region transformation unit 34*a* transforms the target region TAb in the coordinate space of the ultrasound image U into the target region TAa in the data space of the RF signal. Specifically, mathematical transformation from a polar coordinate system of the ultrasound image U as shown in FIG. 3 to an orthogonal coordinate system of the RF signal is performed, and the coordinates corresponding to the designated contour of the object are specified in the coordinate space of the RF signal to set the target region TAa.

The target region specifying unit 34 transmits the information indicating the specified target region TAa to the signal processing unit 16.

The signal processing unit 16 executes normal signal processing, which is signal processing according to the depth of the subject, with respect to the RF signal outside the target region TAa (that is, RF signal in the non-target region NTA) and executes specific signal processing different from the normal signal processing with respect to the RF signal inside the target region TAa.

The normal signal processing is, for example, processing of applying a bandpass filter according to the depth of the subject to the RF signal. For example, as a configuration for the normal signal processing, the signal processing unit 16 includes an evaluator that evaluates a depth change of the RF signal, a smoothing processing unit that smoothens a filter control signal output from the evaluator, a filter processing unit that performs filter processing for each depth, and a filter bank of a filter selection destination that selects a filter based on the filter control signal. Alternatively, the signal processing unit 16 may include a trained model (convolutional neural networks (CNN)) or the like that performs processing of estimating a high SNR signal from a low SNR signal as a configuration for the normal signal processing.

The specific signal processing is, for example, processing of uniformly performing the same processing with respect to the RF signal inside the target region TAa regardless of the depth of the subject. In a case in which the target region specifying unit 34 specifies the type of the object, the signal processing unit 16 executes the specific signal processing according to the specified type of the object with respect to the RF signal inside the target region TAa. Here, the signal processing unit 16 specifies the specific signal processing to be executed, with reference to the processing model DB 30.

As described above, the type of the object and the processing content are associated with each other in the processing model DB 30. The processing content associated with each type of the object represents the content of the specific signal processing that should be executed with respect to the RF signal of the target region TAa corresponding to the object of the type.

For example, in the liver, an abnormality in a liver tissue is found from a non-uniform brightness distribution in a liver tissue image depicted with a uniform texture. Therefore, in the liver tissue image, the image quality in which a speckle signal is smoothly depicted is preferable. In this case, since image quality enhancement in which spatial resolution is more emphasized is required, in the processing model DB 30, image quality enhancement processing in which the spatial resolution is emphasized is associated with the liver. In the image quality enhancement processing in which the spatial resolution is emphasized, for example, the spatial resolution is improved by the signal processing unit 16 performing filter application for improving a pulse characteristic of an ultrasound signal. Further, in order to depict the tissue image more smoothly, the image formation unit 20 performs speckle reduction (smoothing processing) of reducing a speckle pattern.

On the other hand, the kidney is composed of various tissues such as a kidney cortex, a kidney medulla, and a kidney pelvis, and the shading of brightness is more severe than that of the liver. For the founding of the abnormality in the kidney, the image quality with clearer shading is preferable. In this case, since image quality enhancement in which contrast resolution is more emphasized is required, in the processing model DB 30, image quality enhancement processing in which the contrast resolution is emphasized is associated with the kidney. In the image quality enhancement processing in which the contrast resolution is emphasized, for example, the signal processing unit 16 performs filter application for further reducing electrical noise or acoustic noise components that are causes of an extra low-brightness image. Further, image processing of emphasizing the connection of the tissue structures in the kidney is performed in the image formation unit 20. In addition, a processing model stored in the processing model DB may be a trained model generated in advance through machine learning such that appropriate image quality enhancement processing as described above is performed according to the input of the RF signal of a specific region or the organ name.

Figure 4:
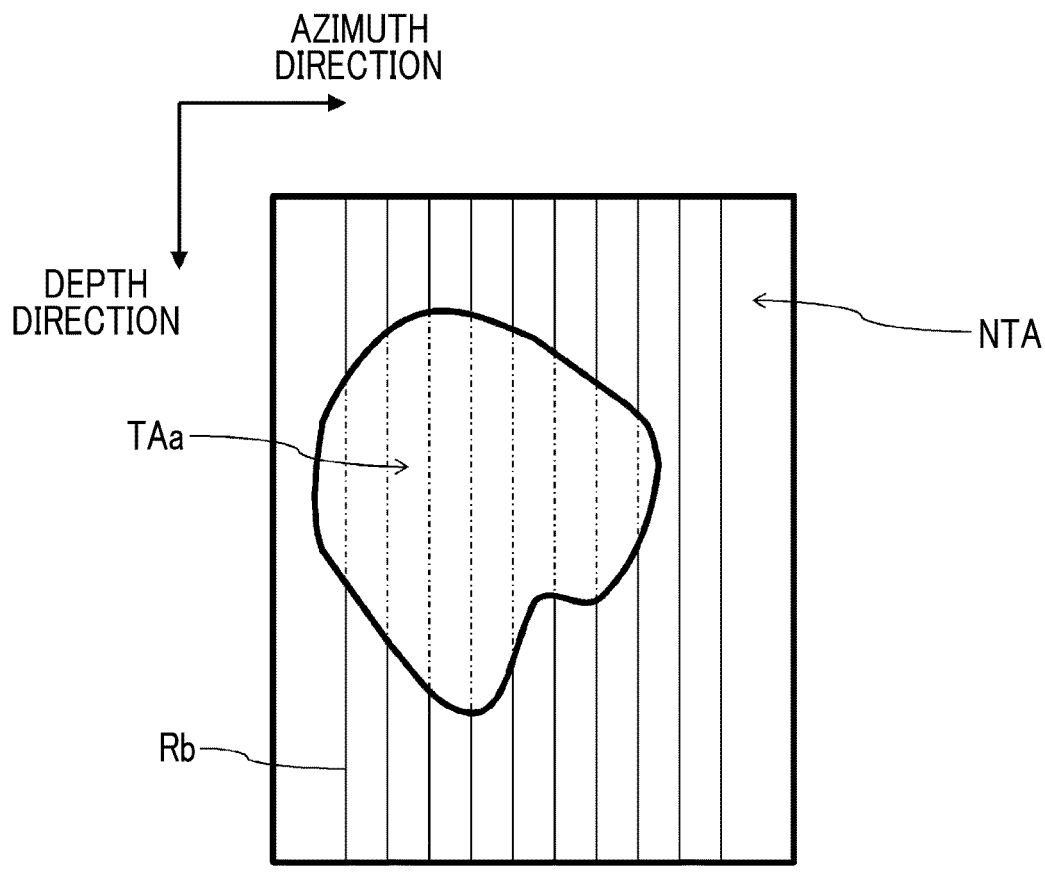
FIG. 4 is a conceptual diagram showing a state in which signal processing, which is different from signal processing with respect to reception beam data outside the target region, is executed with respect to the reception beam data inside the target region.

FIG. 4 shows a state in which the signal processing unit 16 executes the specific signal processing with respect to the RF signal (reception beam data Rb) inside the target region TAa and executes the normal signal processing with respect to the RF signal (reception beam data Rb) in the non-target region NTA. As described above, in the present embodiment, the signal processing unit 16 executes the signal processing, which is different from the signal processing with respect to the non-target region NTA, with respect to the RF signal inside the target region TAa. Here, meaning of different processing includes a case in which the coefficients of the filters are simply different and a case in which the contents of the processing themselves are different.

In addition, for example, in order to prevent a large difference in the brightness at a boundary between the target region TAa and the non-target region NTA, the signal processing unit 16 may perform the smoothing processing of smoothing the signal intensity of the RF signal at the boundary between the target region TAa and the non-target region NTA after the signal processing.

In a case in which the target region specifying unit 34 specifies the object (target region TAa) but cannot specify the type of the object, the signal processing unit 16 may execute predetermined specific signal processing with respect to the RF signal inside the target region TAa. Specific signal processing to be executed in a case in which the type of the object cannot be specified need only also be defined in advance in the processing model DB 30.

In addition, for synthesis processing described later, the signal processing unit 16 may also perform the normal signal processing with respect to the RF signal inside the target region TAa, to hold the RF signal inside the target region TAa subjected to the normal signal processing in the memory 28.

As described above, the image formation unit 20 forms the ultrasound image based on the RF signal subjected to the signal processing by the signal processing unit 16. As a result, it is possible to form the ultrasound image (B-mode image) having a higher image quality than the ultrasound image in the related art.

The image formation unit 20 may synthesize the ultrasound image formed based on the RF signal subjected to the normal signal processing and the ultrasound image formed based on the RF signal subjected to the specific signal processing for the inside of the target region TAa at a synthesis ratio indicated by the user. For example, the display controller 22 displays a slide controller on the display 24, and in a case in which the user shakes the slide controller to one end side, the image formation unit 20 displays the ultrasound image formed based on the RF signal subjected to the specific signal processing for the inside of the target region TAa and the ultrasound image formed based on the RF signal subjected to the normal signal processing for the non-target region NTA in combination on the display 24. On the other hand, in a case in which the user shakes the slide controller to the other end side, the image formation unit 20 combines the ultrasound image formed based on the RF signal subjected to the normal signal processing for the inside of the target region TAa and the ultrasound image formed based on the RF signal subjected to the normal signal processing for the non-target region NTA to display the combined ultrasound image on the display 24. In this case, as in the related-art case, the ultrasound image is formed based on the RF signal subjected to the normal signal processing over the entire ultrasound image. In addition, in a case in which the user sets the slide controller to the middle side, the image formation unit 20 synthesizes the ultrasound image formed based on the RF signal subjected to the specific signal processing and the ultrasound image formed based on the RF signal subjected to the normal signal processing for the inside of the target region TAa according to an amount indicated by the slide controller, and displays the image obtained by synthesizing and the ultrasound image formed based on the RF signal subjected to the normal signal processing for the non-target region NTA in combination on the display 24.

In addition, the image formation unit 20 may execute different image formation processing between the inside of the target region TAa and the non-target region NTA in the ultrasound image formation processing. In this case as well, as in the processing in the signal processing unit 16, for example, uniform image quality enhancement processing in which the spatial resolution is emphasized is executed with respect to the liver, and uniform image quality enhancement processing in which the contrast resolution is emphasized is executed with respect to the kidney.

Figure 5:
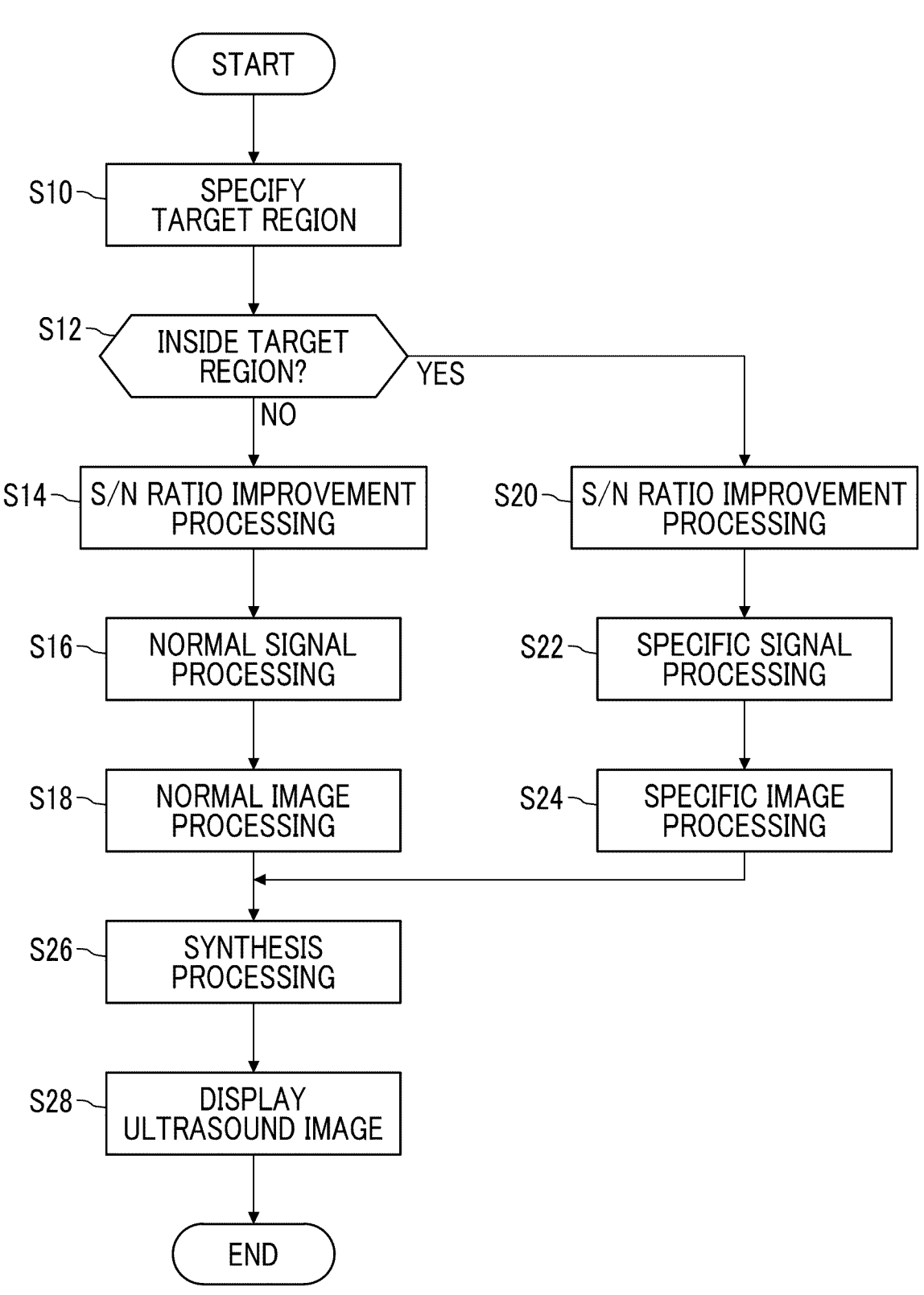
FIG. 5 is a flowchart showing a flow of processing of the ultrasound diagnostic apparatus according to the present embodiment.

The schematic configuration of the ultrasound diagnostic apparatus 10 is described above. It should be noted that each of the units of the transmission/reception unit 14, the signal processing unit 16, the detection processing unit 18, the image formation unit 20, the display controller 22, the target region specifying unit 34, and the region transformation unit 34a is configured of one or a plurality of processors, chips, electric circuits, or the like. Each of these units may be realized by the cooperation between hardware and software. Hereinafter, a flow of the processing of the ultrasound diagnostic apparatus 10 will be described with reference to the flowchart shown in FIG. 5.

In step S10, the target region specifying unit 34 specifies the target region TAa in the data space of the RF signal.

In step S12, the signal processing unit 16 branches the processing between the inside of the target region TAa and the non-target region NTA. The signal processing unit 16 executes the processing with respect to the non-target region NTA in steps S14 to S18, and executes the processing with respect to the target region TAa in steps S20 to S24.

In step S14, the signal processing unit 16 performs SNR improvement according to the signal intensity of the RF signal with respect to the RF signal of the non-target region NTA.

In step S16, the signal processing unit 16 executes the normal signal processing, which is the signal processing according to the depth of the subject, with respect to the RF signal of the non-target region NTA.

In step S18, the image formation unit 20 forms the ultrasound image after executing the normal image processing based on the RF signal of the non-target region NTA.

In step S20, the signal processing unit 16 performs SNR improvement according to the signal intensity of the RF signal with respect to the RF signal of the target region TAa. It should be noted that the signal processing unit 16 also executes the normal signal processing with respect to the RF signal of the target region TAa.

In step S22, the signal processing unit 16 executes the specific signal processing specified based on the processing model DB 30 with respect to the RF signal of the target region TAa.

In step S24, the image formation unit 20 forms the ultrasound image after executing the specific image processing different from the normal image processing based on the RF signal of the target region TAa. It should be noted that the image formation unit 20 forms the ultrasound image after executing the normal image processing based on the RF signal of the target region TAa subjected to the normal signal processing.

In step S26, the image formation unit 20 synthesizes the ultrasound image formed based on the RF signal subjected to the normal signal processing and the ultrasound image formed based on the RF signal subjected to the specific signal processing according to the indication from the user.

In step S28, the display controller 22 displays the formed ultrasound image on the display 24.

Although the embodiment according to the present invention has been described above, the present invention is not limited to the embodiment described above, and various modifications can be made without departing from the gist of the present invention.

For example, in the present embodiment, the ultrasound probe 12 is the probe including the oscillation elements arranged in a row, but the ultrasound probe 12 may be a two-dimension (2D) array probe including oscillation elements arranged in two dimensions. The RF signal, which is the processing target of each of the units of the ultrasound diagnostic apparatus 10, may constitute three-dimensional volume data obtained by the 2D array probe and extending in the depth direction, an azimuth direction, and a slice direction.

What is claimed is:
1. An ultrasound diagnostic apparatus comprising:
a controller configured to:
obtain an RF signal by transmitting and receiving ultrasound waves to and from a subject;
specify a target region corresponding to an object in the subject in a data space of the RF signal by analyzing ultrasound data or based on a user input with respect to an ultrasound image, the ultrasound data being at least one of the RF signal, a coordinate transformation signal obtained by transforming the RF signal into data on a coordinate space of the ultrasound image, and the ultrasound image formed based on the coordinate transformation signal;
execute normal signal processing with respect to the RF signal outside the target region and execute specific signal processing different from the normal signal processing with respect to the RF signal inside the target region, wherein the normal signal processing is signal processing of applying a filter according to a depth of the subject with respect to the RF signal, and wherein the specific signal processing is signal processing of not applying the filter according to the depth of the subject with respect to the RF signal; and
form the ultrasound image based on the RF signal subjected to the normal signal processing and the RF signal subjected to the specific signal processing.
2. The ultrasound diagnostic apparatus according to claim 1,
wherein the controller specifies a type of the object corresponding to the specified target region, and
in a case in which the type of the object is specified, the controller executes the specific signal processing according to the specified type of the object with respect to the RF signal inside the target region.
3. The ultrasound diagnostic apparatus according to claim 2,
wherein in a case in which the type of the object is not specified, the controller executes predetermined specific signal processing with respect to the RF signal inside the target region.
4. The ultrasound diagnostic apparatus according to claim 1, wherein
the controller further transforms the target region, which is specified based on the coordinate transformation signal, the ultrasound image, or the user input, in the coordinate space of the ultrasound image into the target region in the data space of the RF signal.
5. The ultrasound diagnostic apparatus according to claim 1,
wherein the controller also executes the normal signal processing with respect to the RF signal inside the target region, and
synthesizes the ultrasound image formed based on the RF signal subjected to the normal signal processing inside the target region and the ultrasound image formed based on the RF signal subjected to the specific signal processing inside the target region at a synthesis ratio indicated by the user.

* * * * *